United States Patent [19]

Morris

[11] Patent Number: 4,457,026

[45] Date of Patent: Jul. 3, 1984

[54] SURGICAL HEAD DRAPE

[75] Inventor: Henrietta K. Morris, Arlington, Tex.

[73] Assignee: Surgikos, Inc., Arlington, Tex.

[21] Appl. No.: 538,061

[22] Filed: Sep. 30, 1983

[51] Int. Cl.³ .............................................. A42B 00/00
[52] U.S. Cl. ...................................... 2/171; 2/DIG. 7; 2/114; 128/132 D; 128/134
[58] Field of Search ...................... 2/171, DIG. 7, 114; 128/132 D, 163, 134

[56] References Cited

U.S. PATENT DOCUMENTS

| | | | |
|---|---|---|---|
| 3,335,719 | 12/1965 | Boucher | 128/132 D |
| 3,742,994 | 7/1973 | Sense | 128/132 D |
| 3,777,749 | 12/1973 | Collins | 128/132 D |
| 3,911,912 | 10/1975 | Krebs et al. | 128/132 D |
| 3,952,738 | 3/1976 | Krzewinski | 128/132 D |
| 3,955,569 | 5/1976 | Krzewinski et al. | 128/132 D |
| 4,166,461 | 9/1979 | Oliver et al. | 128/132 D |

*Primary Examiner*—Werner H. Schroeder
*Assistant Examiner*—Mary A. Ellis
*Attorney, Agent, or Firm*—Michael Q. Tatlow

[57] ABSTRACT

A surgical drape for use on a patient's head is disclosed. The drape comprises a head sheet for placement on the patient's head and a main sheet for placement under the patient's head. The head sheet has one open end to be wrapped around the patient's head. The opposite end of the head sheet is closed. There are cuffs on both the main sheet and the head sheet for aseptically placing the drape on the patient.

4 Claims, 15 Drawing Figures

FIG-13
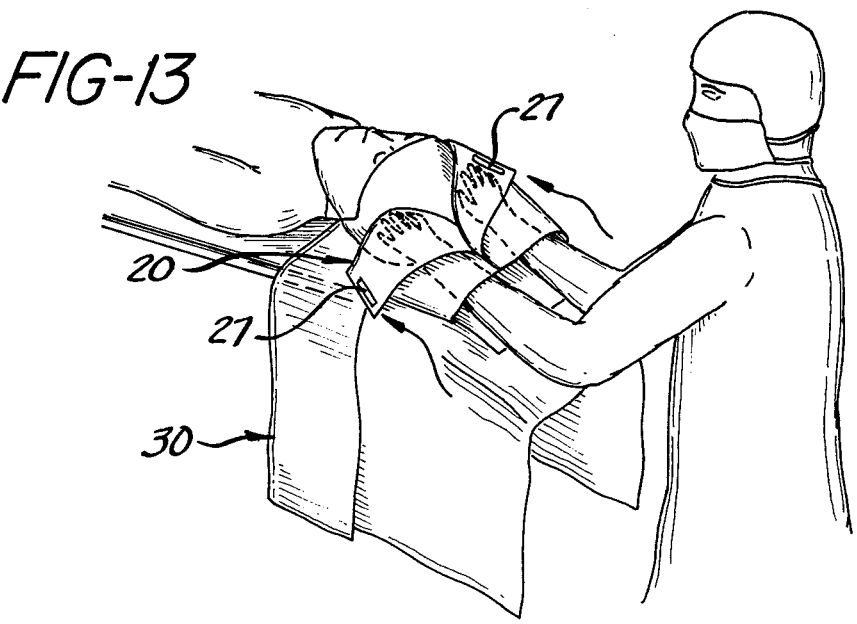
FIG-14
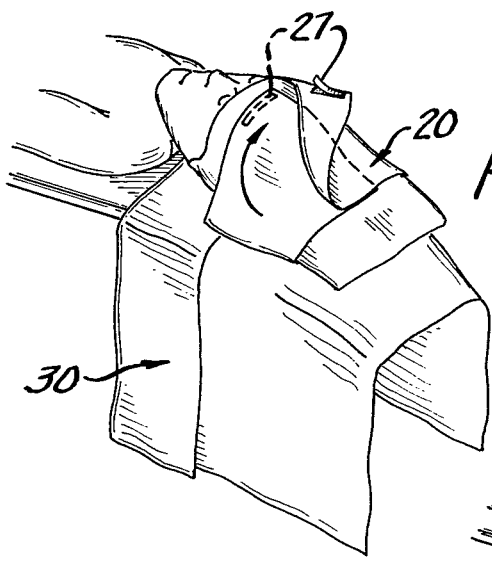
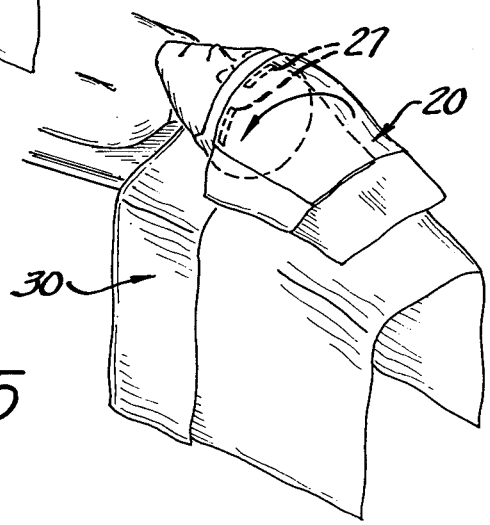
FIG-15

SURGICAL HEAD DRAPE

BACKGROUND OF THE INVENTION

1. Field of the Invention

The present invention relates to single-use surgical drapes and, in particular, to a surgical drape that is used in surgery involving the head. Specifically, the drape finds utility in surgical procedures such as eye surgery, dental surgery, nose surgery, ear surgery and those procedures generally referred to as eye, ear, nose and throat or EENT procedures

2. Description of the Prior Art

Prior to the widespread use of single-use surgical drapes, it was common for the surgical staff to drape the head of a patient by using a number of operating room towels. The patient's head would be draped with a towel, and the towel would be clamped in position with a towel clamp or similar instrument. In these procedures, it is desirable to isolate the top portion of the patient's head from the site of the surgical procedure. The draping procedure is to insure that particles of material on the hair of the patient will not fall into the operative site, as such particles could contain bacteria which could contaminate the surgical wound site. The towels, therefore, had to be securely wrapped around the patient's head, and it is difficult to maintain such security with a towel clamp or similar device.

U.S. Pat. No. 3,955,569 discloses a single-use surgical drape which overcomes some of the problems connected with the use of clamps to secure the surgical drape to the head of a patient. The surgical drape in the aforementioned patent had a main sheet with a cuff at the top end to provide a hand-receiving pocket to allow the drape to be aseptically placed on the head of a patient. A strip of adhesive was on the lower surface of the drape under the cuff, and the adhesive was used to secure the drape in the proper position on the head of a patient. Although this drape was an improvement over the previously used drapes, the drape did not provide for any protection under the head of the patient.

U.S. Pat. No. 3,911,912 discloses a surgical drape which contains two distinct portions. The first portion is adapted to fit under the head of the patient and cover the head portion of the operating room table. On the surface of the first portion was attached a second drape which was used to form a head wrap over the head of the patient. The head wrap portion was a rectangular sheet and contained a strip of adhesive tape to secure the drape in position on the head of a patient. A portion of the second drape was opened at the end and would be closed with towel clamps or similar instruments.

U.S. Pat. No. 4,166,461 discloses a head drape which is made from a single sheet of material and cut and folded in such a way as to provide a table cover and a turban wrap to cover the head of the patient. The turban wrap could then be tape clamped or otherwise secured to the head of the patient. In addition, there is provided an adhesive strip on the bottom surface of the base sheet to enable the drape to be placed directly on the head of the patient.

Drapes of the type described above have also been modified by adding adhesive strips on the lower surface of the secondary draping sheet so that the open end of the turban portion of the drape could be closed.

SUMMARY OF THE INVENTION

It is the object of the present invention to provide a surgical drape for EENT surgical procedures which provides an improved aseptic technique to apply the drape to the patient and which will provide better control of the placing of the drape on the patient, as well as provide a drape with completely closed end without the necessity of using towel clamps, adhesive tapes or similar closure devices.

The drape of the present invention includes a base sheet, which may be aseptically positioned under the head of the patient, and a head sheet, which has a closed end which may also be aseptically wrapped around the forehead of the patient and positioned rapidly in the correct position for the operative procedure.

BRIEF DESCRIPTION OF THE DRAWINGS

FIGS. 13-15 illustrate the placement of the drape on a surgical patient.

DETAILED DESCRIPTION OF THE INVENTION

In the following description, dimensions of the various components of the drape are given as a guideline for the construction of a drape. It should be understood that these dimensions can readily be changed depending on whether or not the drape is constructed for a pediatric patient or an adult patient.

Figure 1:
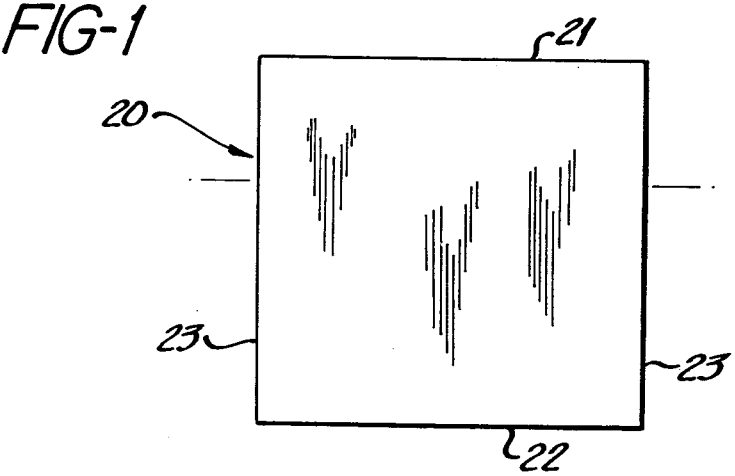
FIG. 1 is a plan view of the sheet of material used to construct the turban or head portion of the drape.
Figure 3:
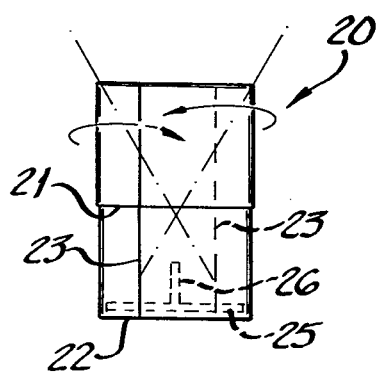
FIG. 3 shows the drape of FIG. 2 folded over to form a tube.
Figure 4:
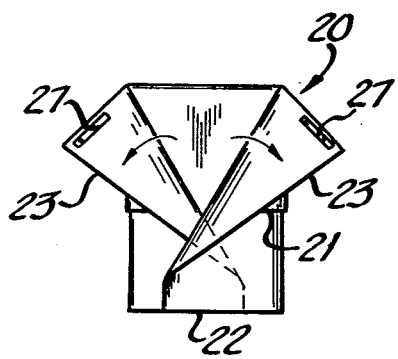
FIG. 4 shows the drape of FIG. 3 folded to form an opening to place the head of the patient and to form the cuffs in the head portion of the drape.

There is shown in FIG. 1 a top plan view of the head sheet 20. The head sheet has a top edge 21, a bottom edge 22 and opposed side edges 23. The overall dimensions of this portion of the drape are approximately 34" wide and 31" from top to bottom. The top edge of the drape is folded backwards onto itself a distance of approximately 12" and secured along lines 24 along the side edges. The edges of the drape are then folded over along two lines spaced approximately 10" from the side edges, and the bottom of the folded over drape is secured with an adhesive or glue line 25, shown in FIG. 3. In addition to the glue line 25, there may be an additional glue line 26 extending along the length of the drape adjacent the bottom edge. The side edges of the drape are then folded from a point spaced between 2" and 4" from the bottom of the drape and at an angle of between 30° and 60° to form an open end of the head sheet. There are adhesive areas 27 along either one or both top edges of the drape which will be used to secure the head sheet to the head of the patient.

Figure 5:
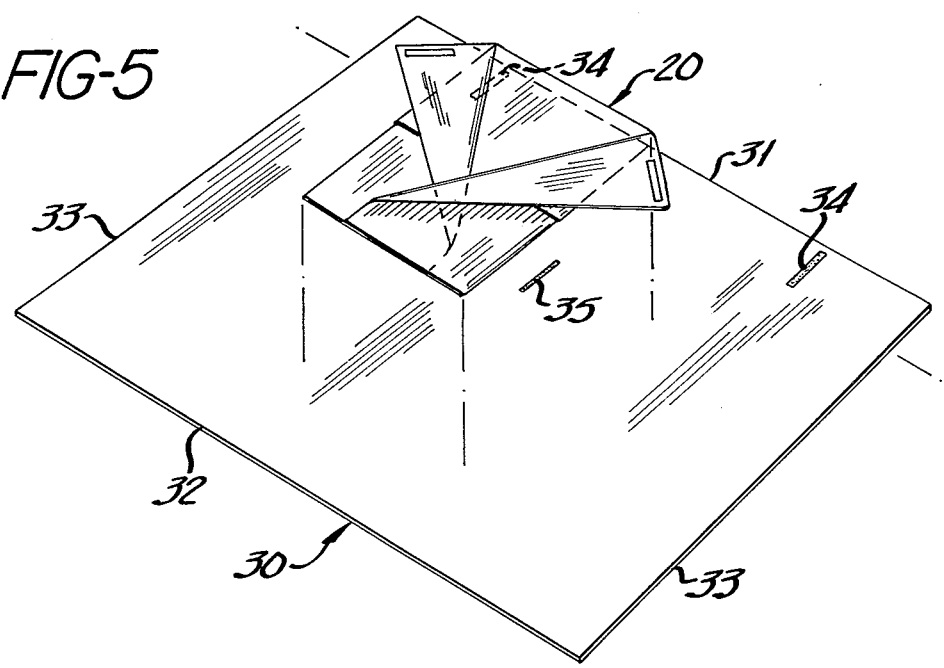
FIG. 5 shows the position of the head sheet of FIG. 4 on the surface of the main sheet of the drape.
Figure 6:
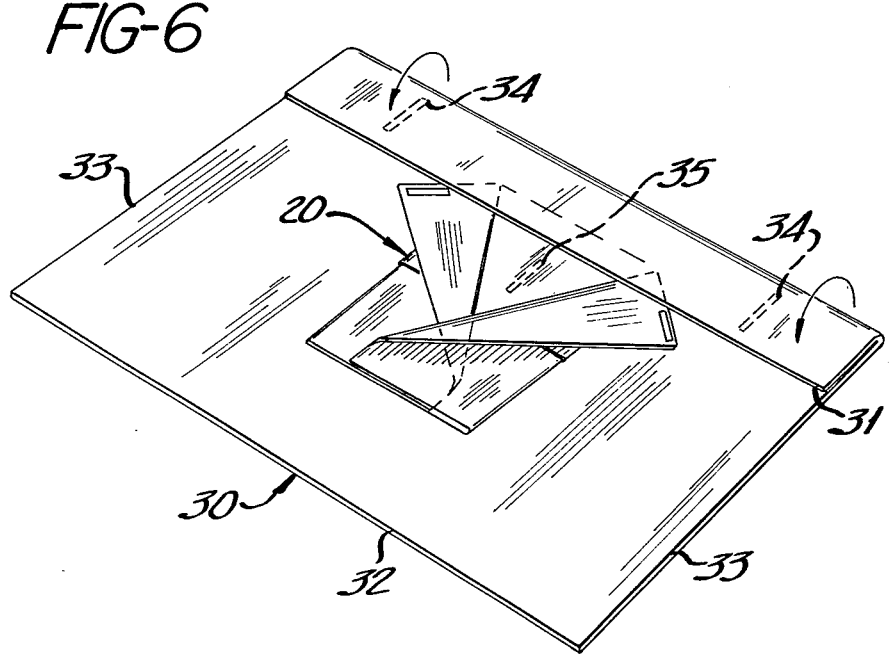
FIG. 6 shows a cuff being formed in the main sheet.
Figure 7:
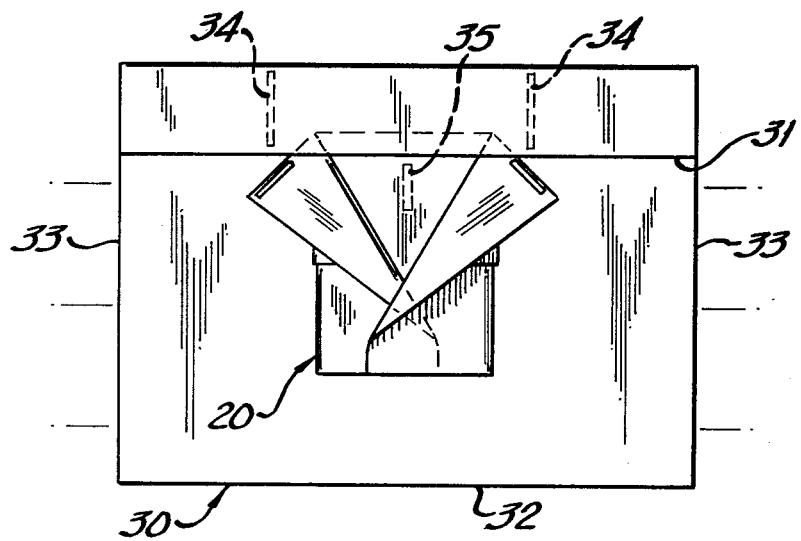
FIG. 7 shows a top plan view of the drape in a fully opened position.

As shown in FIG. 5, the head sheet 20 is positioned on the upper surface of the main sheet 30. The main sheet 30 has a top edge 31, a bottom edge 32 and opposed side edges 33. The top edge 31 of the main sheet is turned onto its upper surface to form a cuff which is held in place by glue lines 34 which are spaced at the side edges of the drape or at a position inward to the side edges but in a position so as to allow the head sheet to be readily removed from under the cuff of the main sheet. The head sheet is secured to the upper surface of the main sheet along a glue line 35. The overall dimensions of the main sheet are approximately 45" wide and 41" long. The cuff at the top edge of the sheet is approximately 6" deep. FIG. 7 shows a top plan view of the head sheet attached to the main sheet. It should be noted that the top of the head sheet underlies the cuff on the main sheet in the preferred construction of the drape. It is also possible to allow the head sheet to overlie the cuff. The purpose of the cuff on the main sheet is to allow the placement of the drape under the head of the patient without any contamination from the patient, since the hands of the surgical staff will be isolated from the patient by the cuff when the drape is placed.

Figure 8:
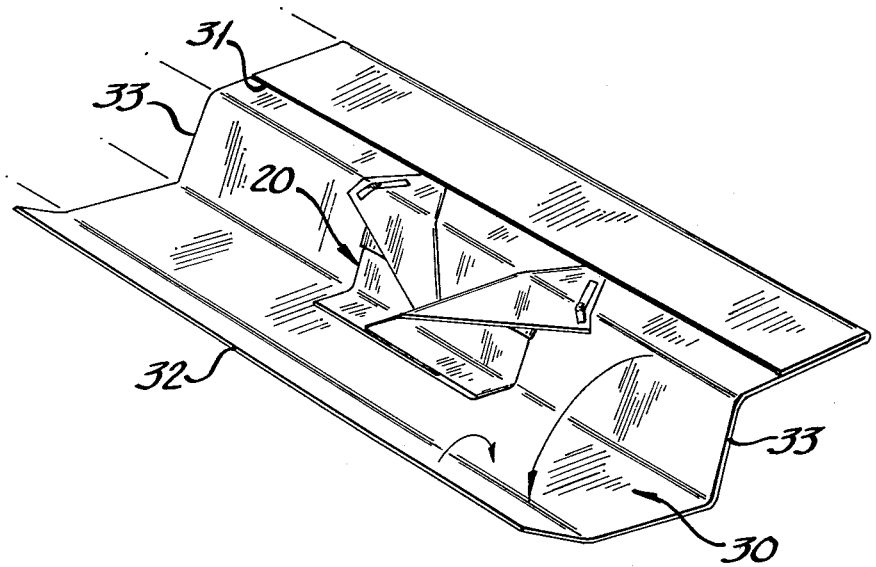
FIGS. 8-12 show the folding sequence to fold the drape into a compact package for sterilization and storage.
Figure 9:
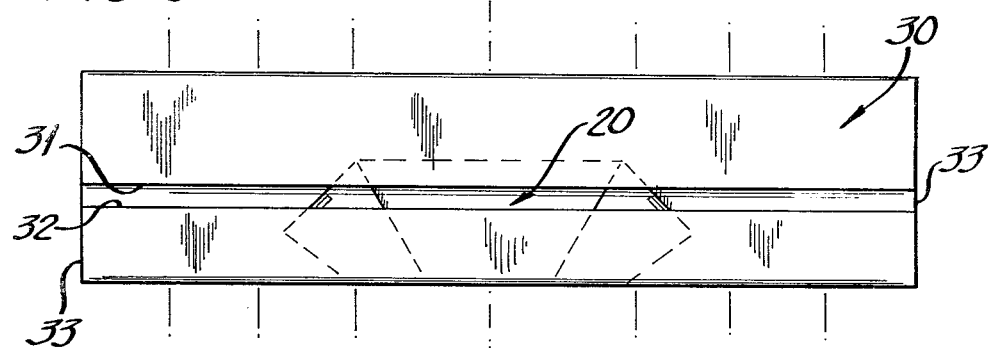
Figure 10:
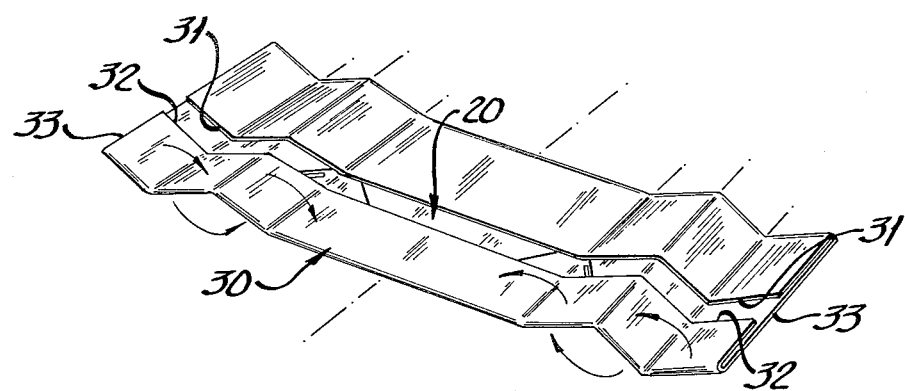
Figure 11:
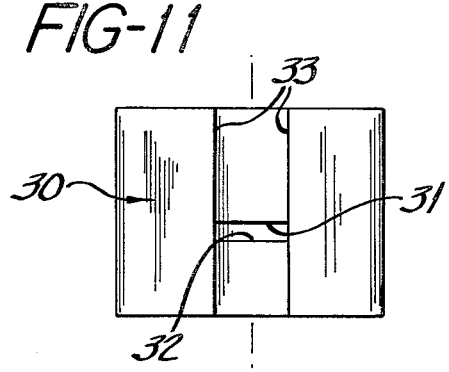
Figure 12:
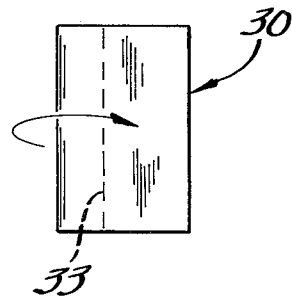

FIG. 8 shows the initial folding sequence of the drape to form a compact package. The drape is folded along transversely extending fold lines to form the configuration shown in FIG. 9. The drape is then fan folded along longitudinally extending fold lines, as shown in FIG. 10, to form the relatively compact package shown in FIG. 11. The last fold of the drape is through the center line of the drape to form the compact package shown in FIG. 12.

Figure 2:
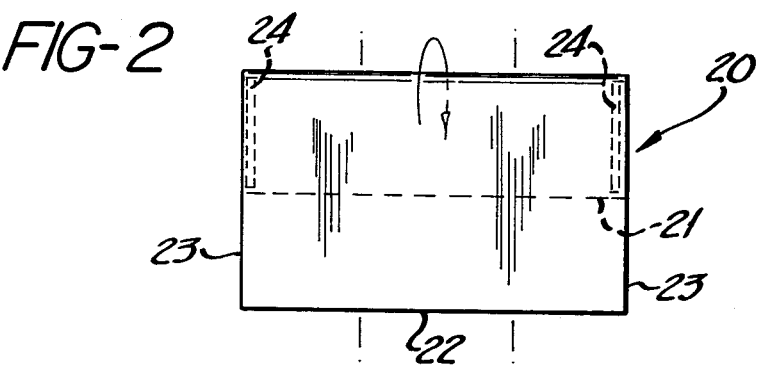
FIG. 2 shows the sheet of FIG. 1 folded over to form a cuff.

FIGS. 13-15 show the placement of the drape on a patient. The first step in the placement of the drape is for the main sheet of the drape to be placed under the head of the patient. A member of the operating room staff will lift the head of the patient, and another staff member will place the main sheet under the head of the patient by putting their hands into the cuff formed in the main sheet by the turned-over top edge which forms the cuff. The placement of the drape in this fashion releases the head sheet, which has a relatively large opening because of the angular folds of the head sheet. The bottom of the patient's head may be easily positioned in the opening so formed. The operating room personnel then close the head sheet portion of the drape which contains a cuff formed by the backward fold of the head sheet shown in FIG. 2. As indicated in FIG. 13, the operating room personnels' hands are placed beneath the wing-folded portions of the drape into the cuffs, and the side edges of the head sheet are then secured around the top portion of the head of the patient and secured in position by the adhesive tapes. It is not necessary to use any other clamps or adhesive securement means to close the lower edge of the drape, since the turban or tubular portion of the drape is closed at the lower end.

I claim:

1. A surgical drape comprising a main sheet having an upper surface and a lower surface, a top edge, a bottom edge and two side edges, a cuff at the top edge of the main sheet being secured to the body of the main sheet by lines of attachment, a head sheet secured to the upper surface of the main sheet adjacent to the top edge of the main sheet, said head sheet having a top edge, a bottom edge and two opposing side edges, a cuff at the top edge of said head sheet, the side edges of the head sheet being overlapped and secured to each other along the bottom edge of the head sheet, the side edges of said head sheet being folded from a point near the bottom edge of said head sheet at an angle of from about 30° to 60° to form an opening, a line of adhesive along the top edge of at least one portion of said head sheet to provide closure means to attach the head sheet around the head of a patient.

2. The drape of claim 1 in which the cuff of said main sheet overlies the top edge of said head sheet.

3. The drape of claim 1 in which lines of attachment of the cuff of the main sheet are spaced inwardly from the side edges of the main sheet.

4. The drape of claim 1 in which there are lines of adhesive on both portions of the top edge of said head sheet.

* * * * *